US008523806B2

(12) United States Patent
Hayakawa

(10) Patent No.: US 8,523,806 B2
(45) Date of Patent: Sep. 3, 2013

(54) SPRAYER

(75) Inventor: Koichi Hayakawa, Ashigarakami-gun (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 644 days.

(21) Appl. No.: 12/402,262

(22) Filed: Mar. 11, 2009

(65) Prior Publication Data

US 2009/0234326 A1    Sep. 17, 2009

(30) Foreign Application Priority Data

Mar. 12, 2008 (JP) ................................ 2008-063265

(51) Int. Cl.
*A61M 37/00* (2006.01)

(52) U.S. Cl.
USPC .................. 604/82; 604/24; 604/68; 604/69; 604/70; 604/264

(58) Field of Classification Search
USPC ................................ 604/24, 82, 264, 68–70
See application file for complete search history.

(56) References Cited

U.S. PATENT DOCUMENTS 4,846,405 A 7/1989 Zimmermann
5,732,885 A * 3/1998 Huffman .................... 239/416.5
5,755,362 A 5/1998 Rodriguez et al.
6,113,571 A * 9/2000 Zinger et al. .................... 604/82
6,165,201 A * 12/2000 Sawhney et al. .............. 606/214
6,464,663 B1 10/2002 Zinger
6,613,020 B1 * 9/2003 Holm et al. .................. 604/191
2003/0187408 A1 10/2003 Marx
2007/0005007 A1 * 1/2007 Hoogenakker et al. ......... 604/82
2008/0272209 A1 11/2008 Yokoyama et al.
2008/0294099 A1 * 11/2008 Yatabe et al. .................. 604/82
2009/0005731 A1 1/2009 Yokoyama

FOREIGN PATENT DOCUMENTS

EP 1 955 660 A 8/2008
GB 1 221 625 A 2/1971
JP 07-100209 A 4/1995
JP 09-296039 A 11/1997
JP 11-502464 A 3/1999
JP 2001-057979 A 3/2001
JP 2001-515401 A 9/2001
JP 2002-282368 A 10/2002
JP 2005-152790 A 6/2005
WO WO 91/03224 A 3/1991
WO WO 95/31138 A1 11/1995

OTHER PUBLICATIONS

U.S. Appl. No. 12/265,498, filed Nov. 5, 2008, Hayakawa.

* cited by examiner

*Primary Examiner* — Kevin C Sirmons
*Assistant Examiner* — Edelmira Bosques
(74) *Attorney, Agent, or Firm* — Buchanan Ingersoll & Rooney PC

(57) ABSTRACT

A sprayer is capable of inhibiting or preventing clogging occurring in a nozzle upon ejection of a liquid through the nozzle. A sprayer includes liquid supply for separately supplying a first liquid and a second liquid different in liquid composition, and a nozzle. The nozzle includes a first flow path and a second flow path along which passes the first liquid and the second liquid supplied from the liquid supply. In addition, the nozzle includes a third flow path along which passes a gas. A merge part is provided at which the first flow path and the second flow path merge at their respective halfway parts. A vent is provided at the merge part for allowing the gas which has passed through the third flow path to flow into the merge part.

21 Claims, 13 Drawing Sheets

SPRAYER

TECHNOLOGICAL FIELD

The present invention generally relates to a device for delivering a liquid material. More specifically, the invention pertains to a sprayer having useful application in the medical field for spraying a liquid at a body region.

BACKGROUND DISCUSSION

Conventionally, there is known a method in which two or more liquids are mixed and ejected to an affected part or the like of a living body to form, for example, an anti-adhesive material, a biological tissue adhesive, etc. Thus, developmental efforts in the area of sprayers have been made.

Such a sprayer is configured to feed components which coagulate upon mixing, such as a thrombin-containing solution and a fibrinogen-containing solution, in a mutually separated manner to the vicinity of the affected part, and to spray them while mixing at the affected part.

One conventional sprayer includes two syringes respectively containing different types of liquids, and a nozzle for mixing the liquids from respective syringes, and spraying the mixture. The sprayer is configured in the following manner. The nozzle is connected to a gas supply source that supplies an aseptic gas so that the liquids are ejected together with the aseptic gas. The nozzle is specifically configured as a double tube structure including two inner tubes positioned in an outer tube. The liquid from one syringe passes through one inner tube while the liquid from the other syringe passes through the other inner tube. During operation, the gas passes between the outer tube and the inner tubes. The distal end openings of the respective inner tubes function as liquid ejection ports for respectively ejecting the liquids. The distal end opening of the outer tube includes the liquid ejection ports disposed in the inside thereof, and functions as a gas ejection port for ejecting gas.

With the nozzle thus configured, upon stopping the liquid ejection operation, the residual pressures in the respective inner tubes cause the liquids to project outward from the liquid ejection ports in the respective inner tubes. In this state, the liquids are mixed with each other so that the liquids coagulate. As a result, clogging occurs in each liquid ejection port. Further, the liquids ejected outward from the liquid ejection ports of respective inner tubes also respectively extend to the gas ejection port. Accordingly, the liquids are also mixed with each other to coagulate at the gas ejection port, resulting in clogging. When spraying is once again tried after the occurrence of clogging, the coagulated liquids inhibit the ejection of the liquids from respective liquid ejection ports, and ejection of the gas from the gas ejection port. Thus, it is difficult to perform respraying.

SUMMARY

A sprayer disclosed here is able to reduce the occurrence of clogging following ejection of liquid from a nozzle. When a liquid is ejected from a nozzle, a gas flows into a liquid flow path through a vent from a gas flow path, and the liquid is ejected together with the gas. Then, when the ejection of the liquid is stopped, the pressure (the residual pressure) in the gas flow path causes the gas to flow into the liquid flow path through the vent. As a result, it is possible to blow off the liquid in the liquid flow path, particularly, in the merge part to the outside. This can prevent the occurrence of clogging in the nozzle with reliability. Further, the gas ejects outwardly from the inside of the liquid flow path together with the liquid. For this reason, it is possible to omit the provision of a gas ejection port for ejecting a gas as with a conventional sprayer. This can simplify, for example, the configuration of the nozzle.

According to one aspect, a sprayer comprises supply means for separately supplying a first liquid and a second liquid comprising different liquid compositions, and a nozzle comprising a first liquid flow path in fluid communication with the supply means and along which the first liquid flows, and a second liquid flow path in fluid communication with the supply means and along which the second liquid flows. The nozzle also comprises a gas flow path for allowing a gas to pass therethrough, and a merge part at which the first flow path and the second flow path merge so that the first liquid flowing along the first liquid flow path mixes with the second liquid flowing along the second liquid flow path to form a mixed liquid. The sprayer also includes at least one vent through which flows the gas which has passed through the gas flow path, with the at least one vent being located at the merge part of the liquid flow path or at a portion on an upstream side of the merge part relative to a direction of flow of the gas.

According to another aspect, a method of applying a mixed liquid to a living body involves supplying a first liquid along a first liquid path to a merge part of a nozzle, and supplying a second liquid along a second liquid path different from the first liquid path to the merge part of the nozzle to mix the first liquid and the second liquid together in the merge part to produce a mixed liquid, with the first and second liquids comprising different liquid compositions. The method further comprises supplying gas to the merge part at a point upstream of an ejection port of the nozzle and/or the first liquid path at a point upstream of a distal end of the first liquid path, and ejecting the mixed liquid and the gas from the ejection port of the nozzle at the living body.

DETAILED DESCRIPTION

FIGS. 1-6 illustrate aspects of a sprayer utilizing a nozzle according to a first embodiment disclosed here. In the description below, for purposes of convenience and facilitating the description, the right hand side in FIGS. 1-6, and similarly for FIGS. 7-15, is referred to as the "proximal end" or "upstream side"; and the left hand side is referred to as the "distal end" or "downstream side".

Figure 1:
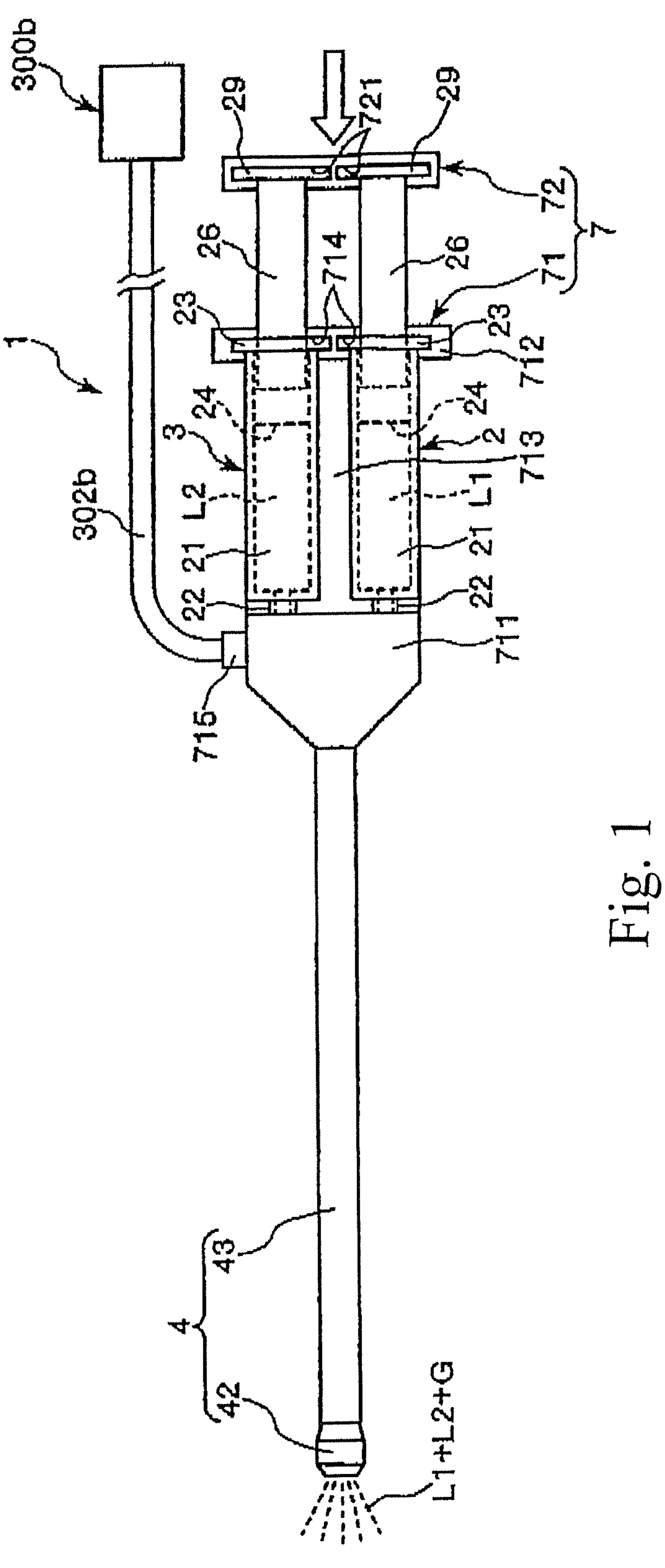
FIG. 1 is a plan view showing a first embodiment of a sprayer disclosed here.

The sprayer 1 shown in FIG. 1 is configured and sized to be inserted into the inside of the abdominal cavity. In addition, the sprayer is adapted to spray, while mixing two kinds of liquids having different liquid compositions (a first liquid L1 and a second liquid L2), the mixture to an organ, the abdominal wall, or the like during, for example, a laparoscopic surgery.

The sprayer 1 is used with a first syringe 2 storing the first liquid L1 and a second syringe 3 for storing the second liquid L2, respectively mounted therein. The first syringe 2 and the second syringe each constitute liquid supply means for storing the respective liquid and for supplying the respective liquid. The first syringe 2 and the second syringe 3 have virtually the same configuration.

The first syringe 2 is filled with the first liquid L1 while the second syringe 3 is filled with the second liquid L2. The first liquid L1 contained in the first syringe 2 and the second liquid L2 contained in the second syringe 3 have different compositions (components) from one another.

Preferably, the first liquid L1 and the second liquid L2 are appropriately selected according to the use of the sprayer 1, the intended purpose, the particular situation, etc. For example, when the liquids L1, L2 are used for administering an anti-adhesive material, one of the first liquid L1 and the second liquid L2 can be a liquid containing carboxymethyl dextrin modified with a succinimidyl group, and the other can be a liquid mixture of sodium carbonate and sodium hydrogencarbonate. Such a combination of the first liquid L1 and the second liquid L2 gelate when the two liquids are mixed together.

Of course, it is to be understood that the types and combinations of the first liquid L1 and the second liquid L2 are not limited to the ones mentioned above by way of example.

Figure 2:
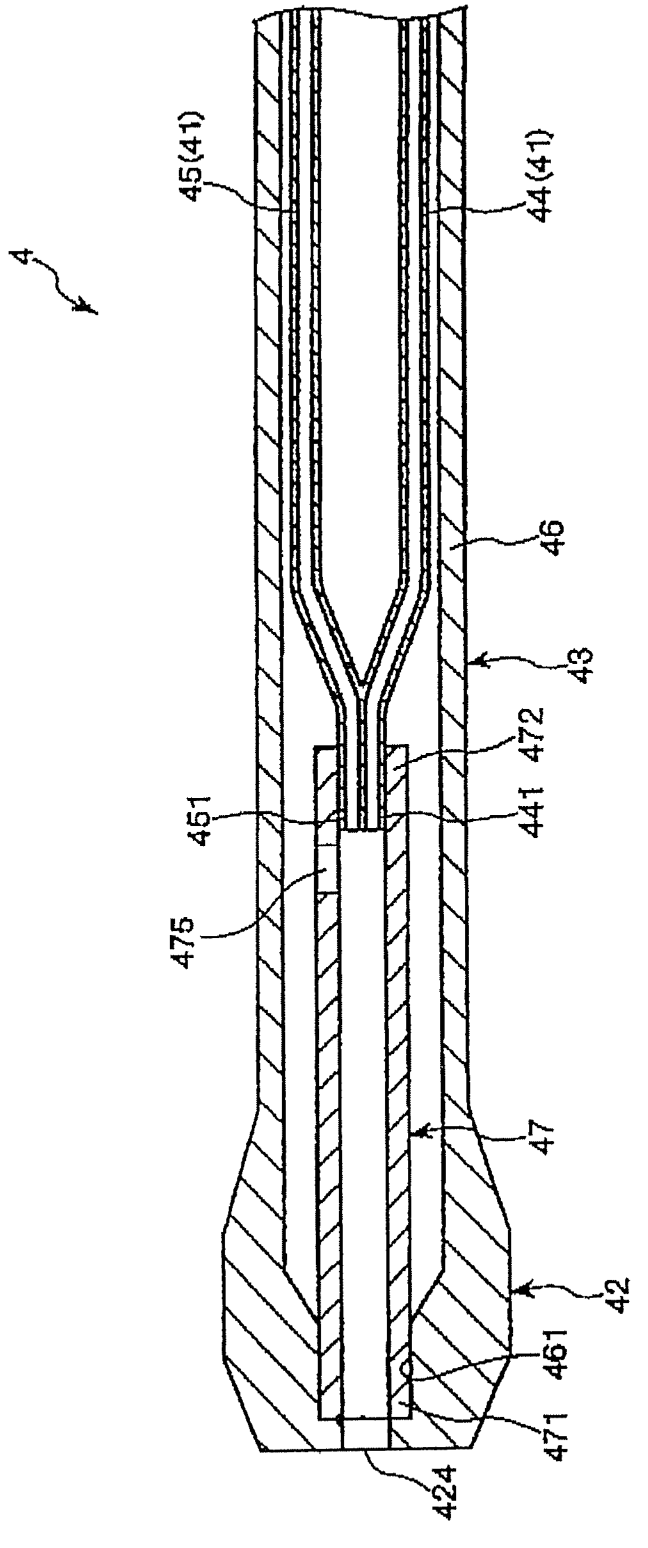
FIG. 2 is a longitudinal cross-sectional view of the distal end part of a nozzle of the sprayer shown in FIG. 1, in one operational state of the sprayer.

The first syringe 2 and the second syringe 3 are respectively connected to a nozzle 4. A respective plunger 26 and gasket 24 is associated with each syringe, and is adapted to be pushed (moved) inwardly and operated. As a result, the first liquid L1 is supplied into a first flow path 44 of the nozzle 4, and the second liquid L2 is supplied into a second flow path 45 of the nozzle 4 as shown in FIG. 2. The pressing operation of each plunger 26 is manually carried out by an operator of the sprayer 1.

Figure 4:
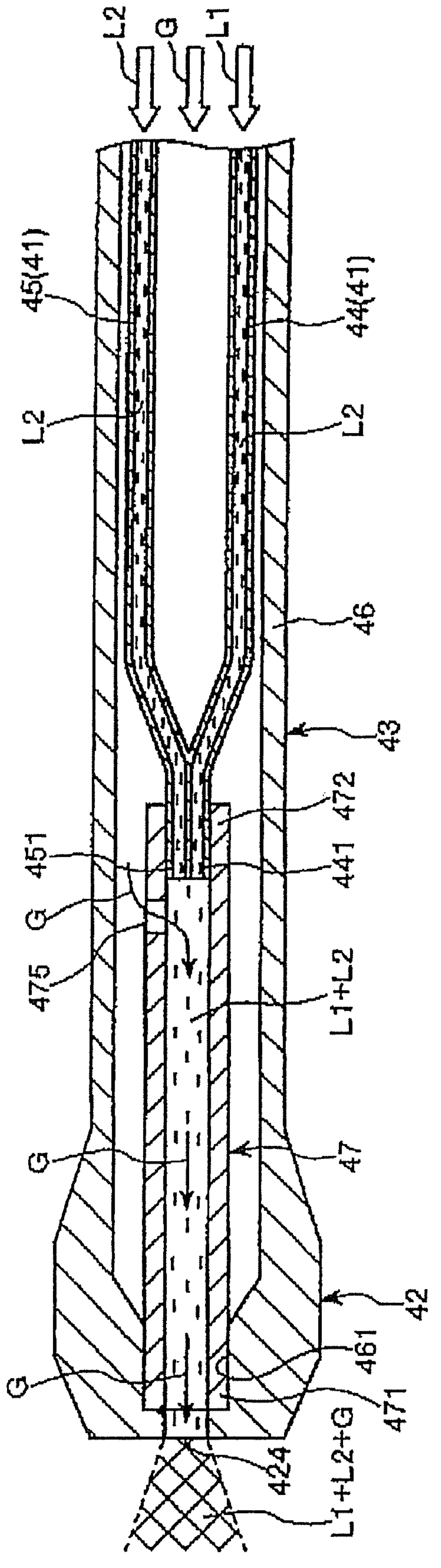
FIG. 4 is a longitudinal cross-sectional view of the distal end part of a nozzle of the sprayer shown in FIG. 1, in another operational state of the sprayer.

Referring generally to FIGS. 1 and 4, the sprayer 1 is configured to eject the first liquid L1 and the second liquid L2 together with an aseptic gas G. The presence of the gas G atomizes the mixture, which enables the mixture to be uniformly sprayed onto the desired site. The gas G is supplied from a gas cylinder 300*b*. The gas cylinder 300*b* is connected to the nozzle 4 via a tube 302*b*.

The gas cylinder 300*b* includes an internal space filled with or containing high pressure gas G. Thus, the gas cylinder 300*b* can supply the gas G flowing at a high speed to the sprayer 1 (nozzle 4). The intermediate part of the gas cylinder 300*b* or the tube 302*b* can be provided with a closable valve for controlling the supply/stoppage of supply of the gas G with respect to the sprayer 1. For spraying the mixture, the valve is rendered in an open state. Examples of the gas G include carbon dioxide.

As shown in FIG. 1, the sprayer 1 includes a sprayer main body 7, and the nozzle 4 located at the distal end side of the sprayer main body 7.

The sprayer main body 7 includes a syringe holding part 71 for holding a barrel 21 of the first syringe 2 and a barrel 21 of the second syringe 3, and a flange joint part 72 holding and joining together a flange 29 of the plunger 26 of the first syringe 2 and a flange 29 of the plunger 26 of the second syringe 3.

The syringe holding part 71 is configured to fix the first syringe 2 and the second syringe 3 in parallel relation. The syringe holding part 71 has a fit part 711 into which an opening part 22 of each barrel 21 is fitted, an insertion part 712 positioned closer to the proximal end side than the fit part 711 and into which the edge of a flange 23 of each barrel 21 is inserted, and a joint part 713 joining the fit part 711 and the insertion part 712.

When the opening part 22 of each barrel 21 is fitted into the fit part 711, the opening part 22 of the first syringe 2 is connected to the first flow path 44 of the nozzle 4, and the opening part 22 of the second syringe 3 is connected to the second flow path 45. This enables supply of the first liquid L1 into the first flow path 44, and supply of the second liquid L2 into the second flow path 45 as generally shown in FIG. 4.

Figure 3:
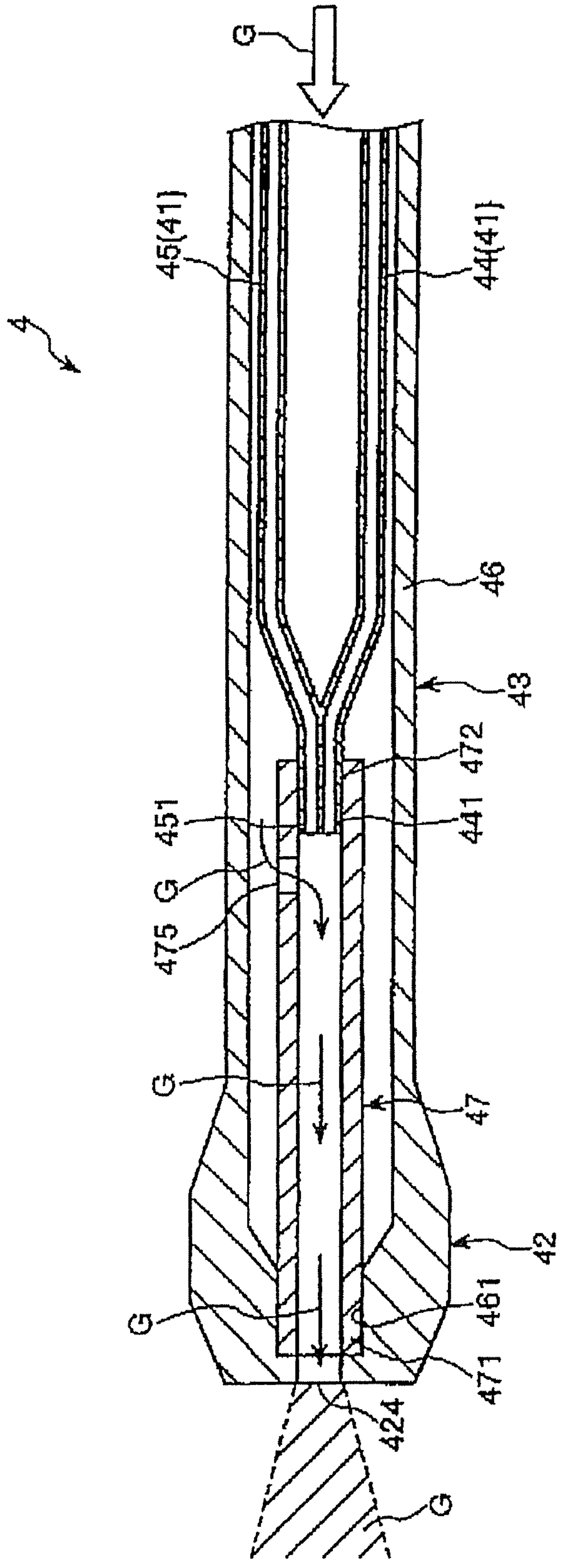
FIG. 3 is a longitudinal cross-sectional view of the distal end part of a nozzle of the sprayer shown in FIG. 1, in another operational state of the sprayer.

The outer circumferential part of the fit part 711 includes a connection part 715 connected with the end of the tube 302*b* through which the gas G from the gas cylinder 300*b* passes. In the illustrated embodiment, the connection part 715 projects outwardly. When the tube 302*b* is connected to the connection part 715, the tube 302*b* is connected to a third flow path (gas flow path) 46 of the nozzle 4. This enables supply of the gas G into the third flow path 46 as generally illustrated in FIGS. 3 and 4.

The insertion part 712 includes a groove 714 into which the edge of the flange 23 of each barrel 21 is inserted.

With the syringe holding part 71, the opening part 22 of each barrel 21 is fitted into the fit part 711, and the flange 23 of each barrel 21 is inserted into the insertion part 712 (groove 714). Thus, each barrel 21 is reliably held by the syringe holding part 71.

The flange joint part 72 is a plate-shaped member interconnecting the flange 29 of the plunger 26 of the first syringe 2 and the flange 29 of the plunger 26 of the second syringe 3. The flange joint part 72 includes a groove 721 into which the edge of the flange 29 of each plunger 26 is inserted or positioned. By pressing the flange joint part 72 toward the direction of the distal end, it is possible to move the respective plungers 26 of both syringes toward the distal end direction in one step (i.e., at the same time). Thus, the flange joint part 72 is an example of an operation part to be pressed and operated by a user when the sprayer 1 is used, i.e., the mixture is sprayed to the objective site such as the affected part.

As shown in FIG. 1, the nozzle 4 is set on the distal end side of the sprayer main body 7. The nozzle 4 is configured to eject a mixture of the first liquid L1 and the second liquid L2 together with the gas G. The nozzle 4 includes an elongated nozzle main body 43, and a nozzle head 42 having a larger diameter than the outer diameter of the nozzle main body 43.

As shown in FIGS. 2-6, the nozzle main body 43 has a liquid flow path 41 including the first flow path 44 through which the first liquid L1 fed from the first syringe 2 passes, and the second flow path 45 through which the second liquid L2 fed from the second syringe 3 passes. Further, the nozzle main body 43 has the third flow path 46 through which the gas G fed from the gas cylinder 300*b* passes.

The first flow path 44 and the second flow path 45 which permit the passage of the respective liquids each include a bore or lumen defined by an inner tube. The proximal end of the inner tube forming the first flow path 44 extends to the position at which it is connected to the opening part 22 of the first syringe 2. In a similar manner, the proximal end of the inner tube forming the second flow path 45 extends to the position at which it is connected to the opening part 22 of the second syringe 3.

The distal end portions of the first flow path 44 and the second flow path 45 merge with each other. The distal end portions of the first and second flow paths 44, 45 merge together at a merge part 47. In the illustrated embodiment, the merge part 47 is in the form of a tubular member.

The merge part 47 may be formed as extensions of the respective inner tubes. Alternatively, the merge part 47 may be formed of a tube body separate from the inner tubes as shown in FIG. 2. The distal end part 471 of the merge part 47 is fitted to the distal end inner circumferential part 461 of the outer tube forming the third flow path 46 which is described in more detail later. Further, the proximal end part 472 of the merge part 47 is fitted to distal end parts 441, 451 of the respective inner tubes forming the first flow path 44 and the second flow path 45, respectively. As a result, the merge part 47 is supported and fixed at its opposite ends.

In the illustrated embodiment, the third flow path 46 through which the gas G passes is comprised of a gap defined by the inner tubes respectively forming the first flow path 44 and the second flow path 45, and the outer tube surrounding the inner tubes (i.e., the outer tube situated on the outer circumferential side of the inner tubes). The proximal end part of the outer tube is connected to the tube 302*b* via the connection part 715 of the sprayer main body 7. Further, the distal end of the outer tube is open, and serves as an ejection port 424 through which the liquid mixture, comprised of the mixed first liquid L1 and the second liquid L2 at the merge part 47, is ejected together with the gas G. By virtue of the liquid mixture being ejected together with the gas G, the liquid mixture is atomized and is thus relatively uniformly sprayed to the objective site. The distal end portion 47 of the tubular merger part 47 is connected to and in fluid communication with the ejection port 424.

Thus, the nozzle 4 is constructed as a double tube structure including two inner tubes and the outer tube. With this configuration, the inner tubes (the first flow path 44 and the second flow path 45) and the outer tube (the third flow path 46) are in parallel positional relation to each other. Thus, as described above, respective tubes can be preferably used as the flow paths. Examples of materials which can be used for forming respective tubes include polyvinyl chloride, polypropylene, polyamide, polyurethane, and polytetrafluoroethylene (PTFE) can be used. Such materials can also be used for the tube part forming the merge part 47.

Figure 5:
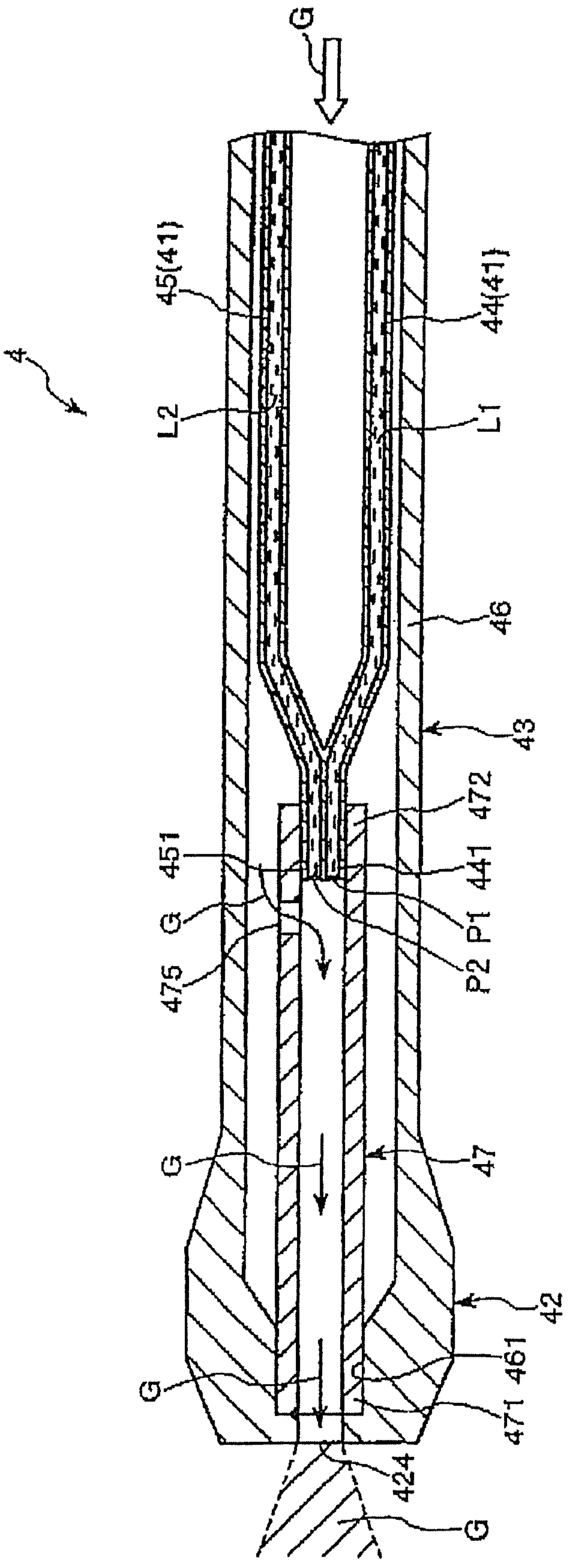
FIG. 5 is a longitudinal cross-sectional view of the distal end part of a nozzle of the sprayer shown in FIG. 1, in another operational state of the sprayer.
Figure 6:
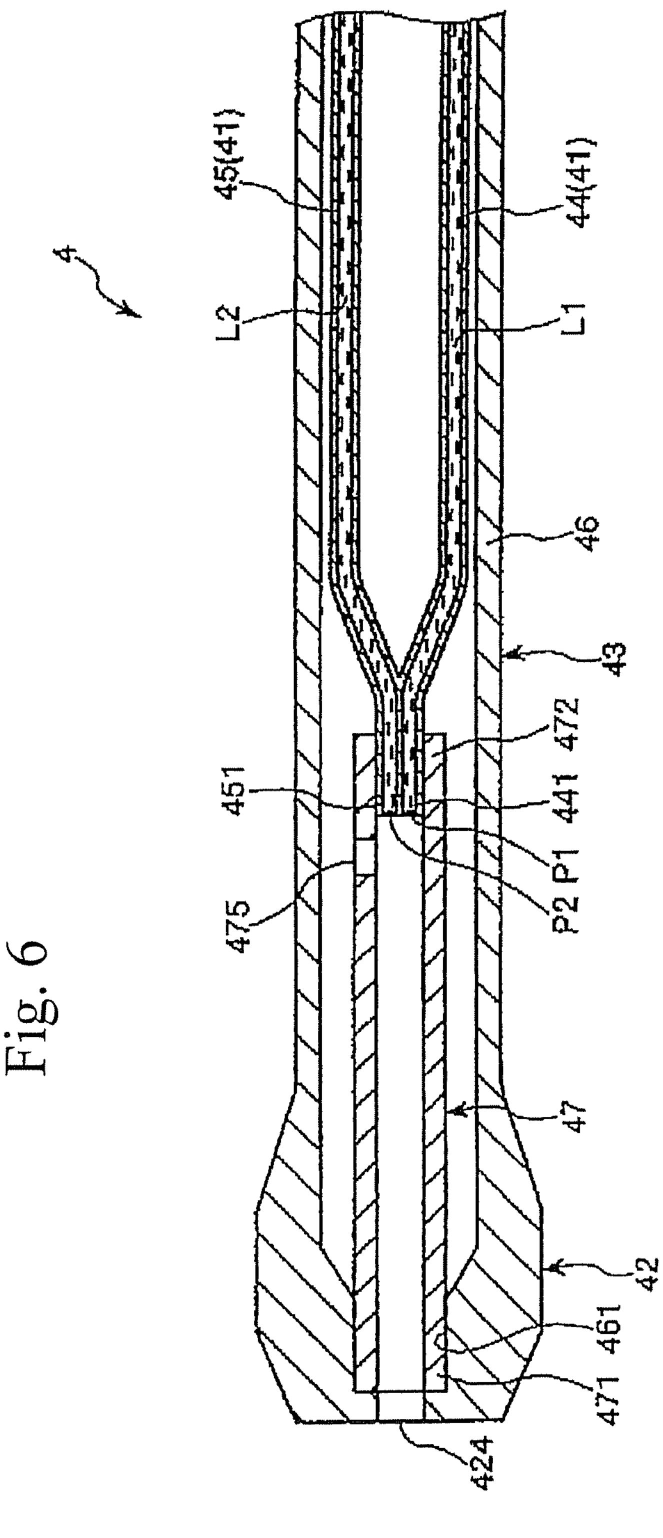
FIG. 6 is a longitudinal cross-sectional view of the distal end part of a nozzle of the sprayer shown in FIG. 1, in an additional operational state of the sprayer.

As shown in FIGS. 2-6, one small through hole or vent 475 is provided in the merge part 47. This one small hole 475 serves as a vent penetrating through the tube wall of the merge part. Through the hole 475, the gas G which has passed through the third flow path 46 can flow into the merge part 47. Accordingly, the flowing gas G is ejected together with the liquid mixture (the first liquid L1 and the second liquid L2) through the ejection port 424 as generally shown in FIG. 4. As a result, the liquid mixture is rendered in an atomized form, and is sprayed to the affected part. Then, as shown in FIG. 5, also for stopping spraying of the liquid mixture, as described later, the gas G flows into the merge part 47 through the inflow hole 475 due to the residual pressure in the third flow path 46. As a result, the residual liquid (liquid mixture) in the merge part 47 is reliably blown off externally from the ejection port 424. This helps prevent the liquid mixture from remaining in the merge part 47, thus preventing the occurrence of clogging in the ejection port 424 (nozzle 4) as shown in FIG. 6.

In the illustrated embodiment, the through hole 475 is preferably situated at a portion on the uppermost stream side of the merge part 47. In this embodiment, the through hole 475 is situated at a portion slightly closer to the distal end side than the portion (the proximal end part 472) to which the distal end part 441 of the first flow path 44 and the distal end part 451 of the second flow path 45 of the merge part 47 are fitted. In other words, the through hole 475 is situated at a position spaced from the distal-most ends of the flow paths 44, 45. As a result, the gas G can spread roughly throughout the merge part 47 through the hole 475 so that the residual liquid in the merge part 47 can be removed with more reliability upon stopping the spraying of the liquid mixture. This helps more reliably prevent clogging from occurring in the ejection port 424 (nozzle 4).

In the operational state shown in FIG. 4, i.e., when the liquid mixture is being ejected, the gas G which has flowed into the merge part 47 through the hole 475 forms microbubbles (air bubbles) in the liquid mixture passing through the merge part 47. Due to the microbubbles, the liquid mixture is stirred in the process of passing through the merge part 47. As a result, the first liquid L1 and the second liquid L2 are relatively uniformly and surely mixed with each other to form a liquid mixture which is then sprayed. When the viscosities of both the liquids are different from each other, the liquids are less likely to be a uniform liquid mixture merely by merging the liquids. However, as described above, the microbubbles exert a stirring action of stirring the first liquid L1 and the second liquid L2, and promoting mixing of the two liquids. This results in a uniform liquid mixture.

In the illustrated embodiment, the through hole 475 is circular in shape. In such a case, the hole diameter of the hole 475 is preferably 0.1 to 1 mm, and more preferably 0.3 to 0.6 mm. This enables the gas G to be supplied in the proper amount into the merge part 47. Accordingly, the liquid mixture ejected from the ejection port 424 is reliably rendered in an atomized form. Further, the liquid mixture can be relatively reliably pushed out of the merge part 47 after the stopping of spraying of the liquid mixture. Further, the gas G which has passed through the small hole 475 can relatively easily form microbubbles (air bubbles) in the liquid mixture. Accordingly, the stirring action is produced with relative ease and reliability.

A method is using the embodiment of the sprayer described above and illustrated in the drawing figures is described below with reference to FIGS. 2-6.

The first syringe 2 and the second syringe 3 contain or are filled with the first liquid L1 and the second liquid L2, respectively, each in an amount necessary for being sprayed onto the affected part. In this operational state, as shown in FIG. 2, the first liquid L1 has not been supplied to the first flow path 44. Similarly, the second liquid L2 has not yet been supplied to the second flow path 45. Further, from the gas cylinder 300*b*, the gas G can be supplied to the sprayer 1. However, the closable valve (cock) for controlling supply/stopping of supply of the gas G with respect to the sprayer 1 is in a closed state. For this reason, the gas G is also not yet supplied to the third flow path 46. Therefore, the liquid mixture is not yet ejected from the nozzle 4.

Then, from the operational state shown in FIG. 2, the valve is rendered in an open state. The gas G is then supplied to the third flow path 46 via the tube 302*b*. As a result, as shown in FIG. 3, the gas G flows into the merge part 47 via the small hole 475, passes through the merge part 47, and is ejected from the ejection port 424.

Next, the operator or user presses the flange joint part 72 of the sprayer 1 so that the flange joint part 72 is operated in the direction of the arrow in FIG. 1. This operation of the flange joint part 72 causes the first liquid L1 to be supplied to the first flow path 44 and the second liquid L2 to be supplied to the second flow path 45 as illustrated in FIG. 4.

The continued operation (pressing or pushing) of the flange joint part 72 of the sprayer 1 causes the first liquid L1 and the second liquid L2 to flow into the merge part 47, merge, and become mixed together. Also, the gas G continues to flow into the merge part 47 via the small hole 475 as described above. Then, from the ejection port 424, the liquid mixture is ejected together with the gas G as indicated in FIG. 4. The liquid mixture is atomized by the gas G, ejected at a relatively high speed, and is sprayed onto the affected part.

After completion of spraying of a prescribed amount of the liquid mixture onto the affected part, the cock is rendered in a closed state again, and the pressing or pushing (operation) on the flange joint part 72 of the sprayer 1 is stopped. As a result, supply of the first liquid L1 to the first flow path 44 is stopped, and supply of the second liquid L2 to the second flow path 45 is stopped.

Further, the supply of gas G to the third flow path 46 is also stopped. However, the gas G continues to flow into the merge part 47 by virtue of the residual pressure in the third flow path 46. As a result, in the merge part 47, the liquid mixture is pushed out of the ejection port 424 by the gas G which has flowed in via the through hole 475 as depicted in FIG. 5. As a result, a distal end P1 of the first liquid L1 (i.e., the distal-most location of the first liquid L1) is situated in the vicinity of the distal end part 441 of the first flow path 44, and a distal end P2 of the second liquid L2 is situated in the vicinity of the distal end part 451 of the second flow path 45 (i.e., the distal-most location of the second liquid L2). With such a configuration, the liquid mixture is prevented from remaining in the merge part 47, particularly, in the vicinity of the ejection port 424. Further, the liquid mixture is prevented from gelatinizing. This helps prevent clogging from occurring in the ejection port 424.

Further, with a decrease in pressure in the third flow path 46, the amount of gas G flowing into the merge part 47 also decreases. Finally, the flow of gas g is also stopped as shown in FIG. 6.

Thus, with this disclosed and illustrated embodiment of the sprayer 1, clogging is prevented from occurring in the nozzle 4. Therefore, the sprayer 1 can be used again at a later time for spraying onto the affected part.

Incidentally, after completion of spraying of a prescribed amount of the liquid mixture onto the affected part, as described above, the cock is rendered in a closed state again. However, the invention is not limited in this regard as the cock may also be left in an open state.

Figure 7:
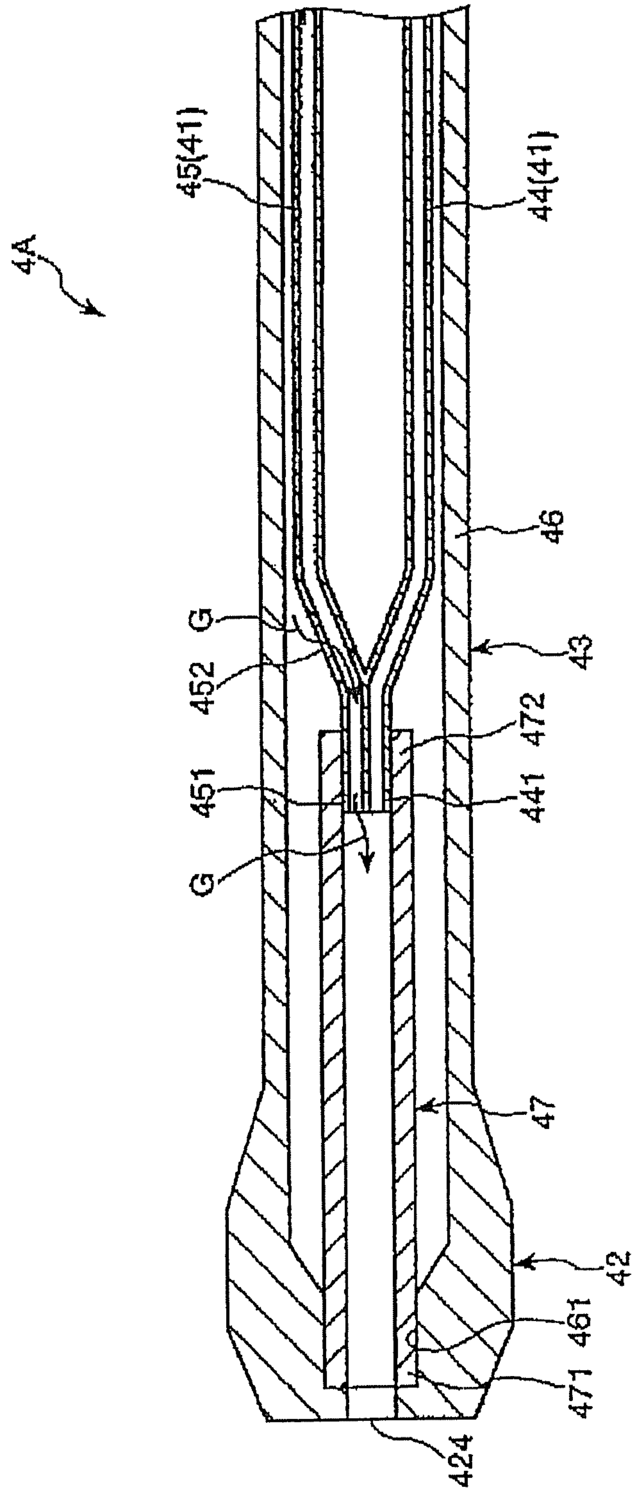
FIG. 7 is a longitudinal cross sectional view of the distal end part of the nozzle of a sprayer according to a second embodiment.

FIG. 7 illustrates the distal end part of the nozzle in a sprayer according to a second embodiment.

The following description of the second embodiment of the sprayer focuses primarily upon the differences between this second embodiment and the embodiment described above. Features associated with this second embodiment that are the same as those associated with the first embodiment are identified by common reference numerals and a detailed description of such features is not repeated. This embodiment is the same as the first embodiment except that the position at which each inflow hole is formed is different.

In the nozzle 4A shown in FIG. 7, an inflow hole or vent 452 is formed in a part of the second flow path 45 at a position upstream of the merge part 47 of the liquid flow path 41. The inflow hole 452 is situated in the vicinity of the distal end part 451 (the portion on the downstream side) of the second flow path 45.

With such a configuration, the gas G passes through the inflow hole 452 and the distal end part 451 of the second flow path 45 sequentially, and flows into the merge part 47. The gas G flowing into the merge part 47 can spread roughly throughout the merge part 47. Accordingly, upon stoppage of the spraying of the liquid mixture, the residual solution in the merge part 47 can be removed with reliability. This can relatively reliably help prevent clogging from occurring in the ejection port 424 (nozzle 4A).

Figure 8:
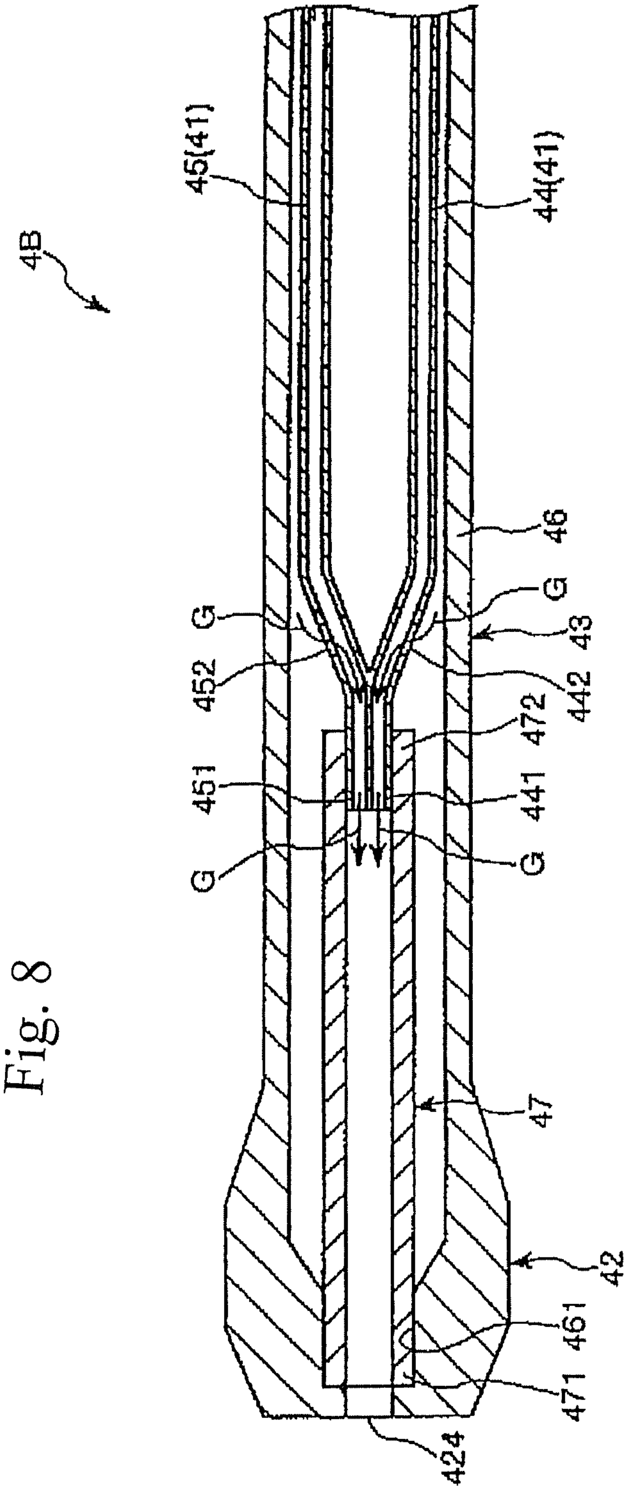
FIG. 8 is a longitudinal cross-sectional view of the distal end part of the nozzle of a sprayer according to a third embodiment.

FIG. 8 illustrates the distal end part of the nozzle in a sprayer according to a third embodiment.

The description below of the third embodiment of the sprayer focuses primarily upon the differences between this third embodiment and the embodiments described above. Features associated with this third embodiment that are the same as those associated with the embodiments described above are identified by common reference numerals and a detailed description of such features is not repeated.

This embodiment is the same as the second embodiment except that the number of inflow holes and the position at which each inflow hole is formed are different.

The nozzle 4B shown in FIG. 8 includes, in addition to the inflow hole or vent 452 in the second flow path 45, an inflow hole or vent 442 formed in a part of the first flow path 44. The inflow hole 442 is located on the upstream side of the merge part 47 of the liquid flow path 41. The inflow hole 442 is disposed in the vicinity of the distal end part 441 (the portion on the downstream side) of the first flow path 44. The inflow hole 442 is located along the first flow path 44 at a position symmetric to the location of the inflow hole 452 with respect to the axis of the nozzle 4B.

With such a configuration, the gas G which has sequentially passed through the inflow hole 452, and the distal end part 441 of the first flow path 44, and the gas G which has sequentially passed through the inflow hole 452, and the distal end part 451 of the second flow path 45 flow into the merge part 47. For this reason, in the nozzle 4B, the amount of the gas G to flow into the merge part 47 is larger than with the nozzle 4A of the second embodiment. Therefore, upon stopping spraying of the liquid mixture, the residual liquid in the merge part 47 can be removed with more reliability. This can help more reliably prevent clogging from occurring in the ejection port 424 (nozzle 4B).

Figure 9:
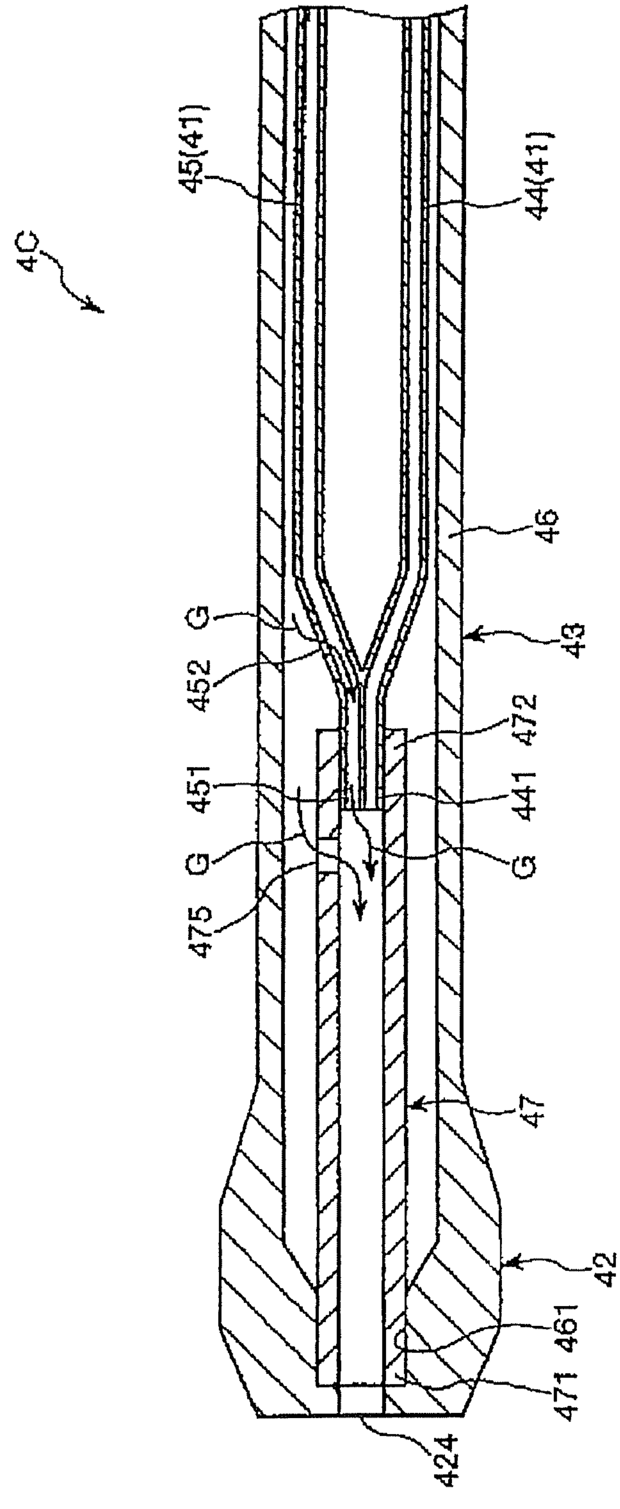
FIG. 9 is a longitudinal cross-sectional view of the distal end part of the nozzle of a sprayer according to a fourth embodiment.

FIG. 9 illustrates the distal end part of the nozzle in a sprayer according to a fourth embodiment.

The description below of this further embodiment of the sprayer focuses primarily upon the differences between this fourth embodiment and the embodiments described above. Features associated with this embodiment that are the same as those associated with the embodiments described above are identified by common reference numerals and a detailed description of such features is not repeated.

This fourth embodiment is the same as the first embodiment except that the number of inflow holes formed and the position at which each inflow hole is formed are different.

The nozzle 4C shown in FIG. 9 includes, in addition to the through hole (vent) 475 located in the merge part 47, the inflow hole (vent) 452 formed in a part of the second flow path 45 on the upstream side of the merge part 47 of the liquid flow path 41. The inflow hole 452 is situated in the vicinity of the distal end part 451 (the portion on the downstream side) of the second flow path 45.

This embodiment of the sprayer is configured so that the gas G which has passed through the inflow hole 452 and the distal end part 451 of the second flow path 45 sequentially merges with the gas G flowing through the hole 475 at the merge part 47. Thus, in this embodiment, the configuration of the nozzle 4C results in a larger amount of gas G flowing into the merge part 47 than with the nozzle 4 of the first embodiment. Therefore, upon stopping the spraying of the liquid mixture, the residual liquid in the merge part 47 can be removed with more reliability. This can help further prevent clogging from occurring in the ejection port 424 (nozzle 4C).

In this embodiment of the nozzle 4C, the same inflow hole 442 as in the third embodiment may be formed in the first flow path 44 at a position on the upstream side of the merge part 47 of the liquid flow path 41.

Figure 10:
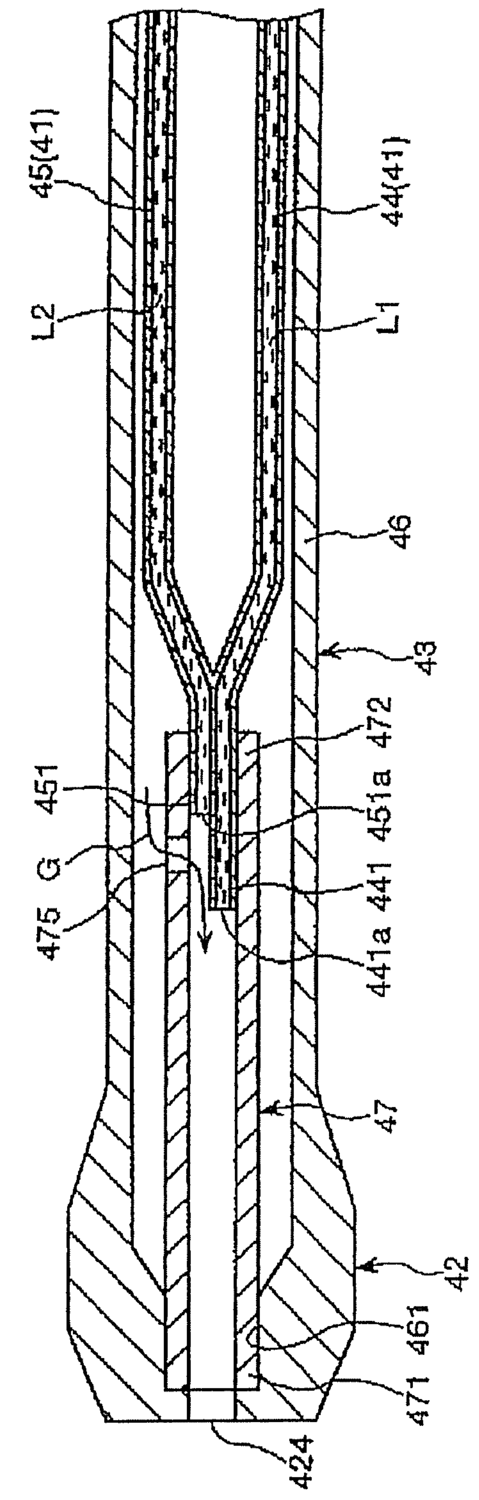
FIG. 10 is a longitudinal cross-sectional view of the distal end part of the nozzle of a sprayer according to a fifth embodiment.

FIG. 10 illustrates the distal end part of the nozzle in a sprayer according to a further embodiment.

The description below of the fifth embodiment of the sprayer focuses primarily upon the differences between this embodiment and the embodiments described above. Features associated with this fifth embodiment that are the same as those associated with the embodiments described above are identified by common reference numerals and a detailed description of such features is not repeated.

This embodiment is the same as the first embodiment except for differences in the configuration of the liquid flow path.

With a nozzle 4D shown in FIG. 10, the position of the open end 441*a* of the first flow path 44 (distal end part 441) facing the merge part 47 is situated closer to the distal end side than the position of the opening end 451*a* of the second flow path 45 (distal end part 451) facing the merge part 47. Namely, the opening end 441*a* of the first flow path 44 and the opening end 451*a* of the second flow path 45 are formed at positions shifted from each other in the longitudinal direction of the nozzle 4D. Thus, the distal-most end 441*a* of the first flow path 44 is positioned distally forward of the distal end 451*a* of the second flow path 45.

As described above, when the spraying operation of the liquid mixture is performed, and the spraying operation is then stopped, the gas G which has flowed into the merge part 47 by the residual pressure can blow off the liquid mixture in the merge part 47 through the ejection port 424. This helps prevent the liquid mixture from remaining in the merge part 47. Accordingly, coagulation of the liquid mixture in the merge part 47 is avoided or prevented, thereby inhibiting or preventing clogging in the ejection port 424. Further, in this embodiment, even when the first liquid L1 involuntarily flows through the opening end 441*a* of the first flow path 44, and the second liquid L2 also involuntarily flows through the opening end 451*a* of the second flow path 45 into the merge part 47, the flowing first liquid L1 and the second liquid L2 can be prevented from being mixed with reliability due to the positioning of the open ends 441*a*, 451*a* at positions shifted from each other along the longitudinal direction of the nozzle 4D. As a result, coagulation of these two liquids in the merge part 47 is avoided or prevented so that clogging in the ejection port 424 does not occur.

In this illustrated embodiment, the small hole (vent) 475 is situated between the opening end 441*a* of the first flow path 44 and the opening end 451*a* of the second flow path 45 with respect to the longitudinal direction of the nozzle 4D (liquid flow path 41) in the configuration shown. However, the sprayer is not limited to this positioning of the hole 475. The small hole 475 may be situated closer to the proximal end side than the opening end 451*a* of the second flow path 45.

Figure 11:
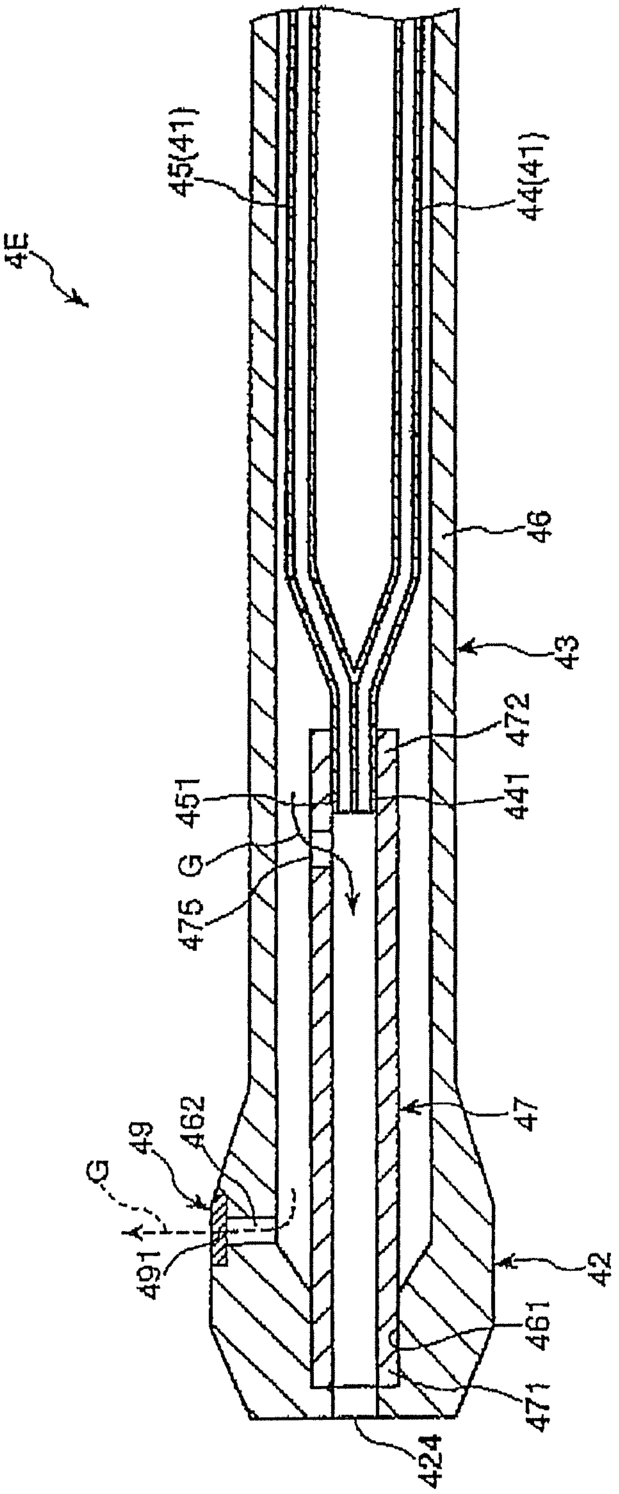
FIG. 11 is a longitudinal cross-sectional view of the distal end part of the nozzle of a sprayer according to a sixth embodiment.

FIG. 11 illustrates the distal end part of the nozzle in a sprayer according to a sixth embodiment.

The description below of this additional embodiment of the sprayer focuses primarily upon the differences between this sixth embodiment and the embodiments described above. Features associated with this embodiment that are the same as those associated with the embodiments described above are identified by common reference numerals and a detailed description of such features is not repeated.

This sixth embodiment is the same as the first embodiment except that the sprayer further includes a pressure adjusting means.

The nozzle 4E shown in FIG. 11 includes a side hole 462. This side hole 462 is located in the outer circumferential part (wall) of the third flow path 46 (nozzle head 42). The side hole 462 penetrates through the outer circumferential part (wall) of the nozzle head 42. A valve body 49 is set in the side hole 462. The valve body 49 functions as a pressure adjusting means for adjusting the pressure in the third flow path 46. The manner in which the valve body 49 is fixed in place is not particularly limited. However, examples may include a method by fitting as shown and a method by adhesion.

The valve body 49 is formed of an elastic body in the form of a disk, and forms a part of the wall part of the third flow path 46. The valve body 49 includes a slit (through hole) 491 penetrating through the valve body 49 in the direction of thickness of the valve body. The valve body 49 is formed of an elastic material, and hence the slit 491 has self closing properties. Due to the self closing property, when spraying of the liquid mixture is not being performed, the slid 491 is closed. This brings the nozzle 4 into the state in which the inside of the third flow path 46 (nozzle 4) and the outside of the third flow path 46 are blocked from each other. In this operational state, the sterility in the third flow path 46 is maintained. When the pressure in the third flow path 46 exceeds a given value while spraying of the liquid mixture is being performed, the slit 491 is pressed under the pressure and is thus opened. This brings the nozzle 4E into the operational state in which the inside of the third flow path 46 (nozzle 4) and the outside of the third flow path 46 communicate with each other via the opened slit 491. In this operational state, a part of the gas G in the third flow path 46 flows out (is discharged) from the opened slit 491. As a result, the pressure inside the third flow path 46 is reduced so that the pressure in the third flow path 46 is adjusted. In the nozzle 4E, the opened slit 491 may also serve as a discharge hole (vent).

When the nozzle distal end of the sprayer 1 comes in contact with biological tissue, and the outlet is blocked, the gas G flowing into the merge part 47 via the small hole 475 may thrust back the first liquid L1 in the first flow path 44 and the second liquid L2 in the second flow path 45. However, with the presence of the valve body 49, the pressure in the third flow path 46 is adjusted, which can prevent such counterflow.

In the illustrated embodiment, the valve body 49 is in the shape of a disk. However, the invention is not limited in this regard. For example, a duckbill valve is also acceptable.

Figure 12:
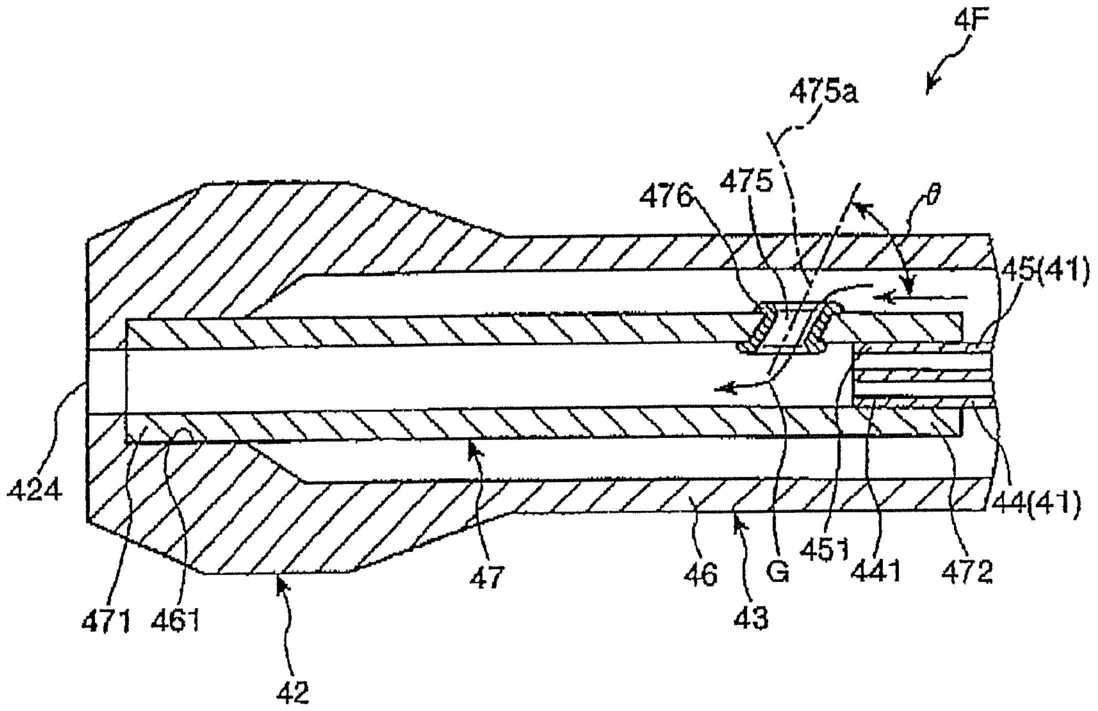
FIG. 12 is a longitudinal cross-sectional view of the distal end part of the nozzle of a sprayer according to a seventh embodiment.

FIG. 12 illustrates the distal end part of the nozzle in a sprayer according to a seventh embodiment.

The description below of the seventh embodiment of the sprayer focuses primarily upon the differences between this embodiment and the embodiments described above. Features associated with this seventh embodiment that are the same as those associated with the embodiments described above are identified by common reference numerals and a detailed description of such features is not repeated.

This embodiment is the same as the first embodiment except that the shape of the inflow hole is different.

The embodiment of the nozzle 4F shown in FIG. 12 includes a small through hole (vent) 475 which is inclined so that the angle θ of the central axis 475*a* of the hole 475 with respect to the liquid flow direction in the merge part 47 (liquid flow path 41) forms an acute angle. As a result, the gas G flowing into the merge part via the angled through hole 475 can flow preferentially toward the ejection port 424, i.e., toward the direction in which the liquid mixture is thrust outward or ejected. As a result, upon stopping spraying of the liquid mixture, the residual liquid in the merge part 47 can be more reliably removed. Accordingly, it is possible to more surely prevent clogging from occurring in the ejection port 424 (nozzle 4F).

Further, the inner circumferential surface and the edge of the hole 475 are provided with a water repellent layer 476. The water repellent layer 476 makes the liquid mixture in the merge part 47 less likely to flow into the third flow path 46 via the hole 475.

The method for forming the water repellent layer 476 is not particularly limited. Examples may include a method in which a material having water repellency (e.g., polytetrafluoroethylene (PTFE)) is sprayed in the vicinity of the through hole 475.

Figure 13:
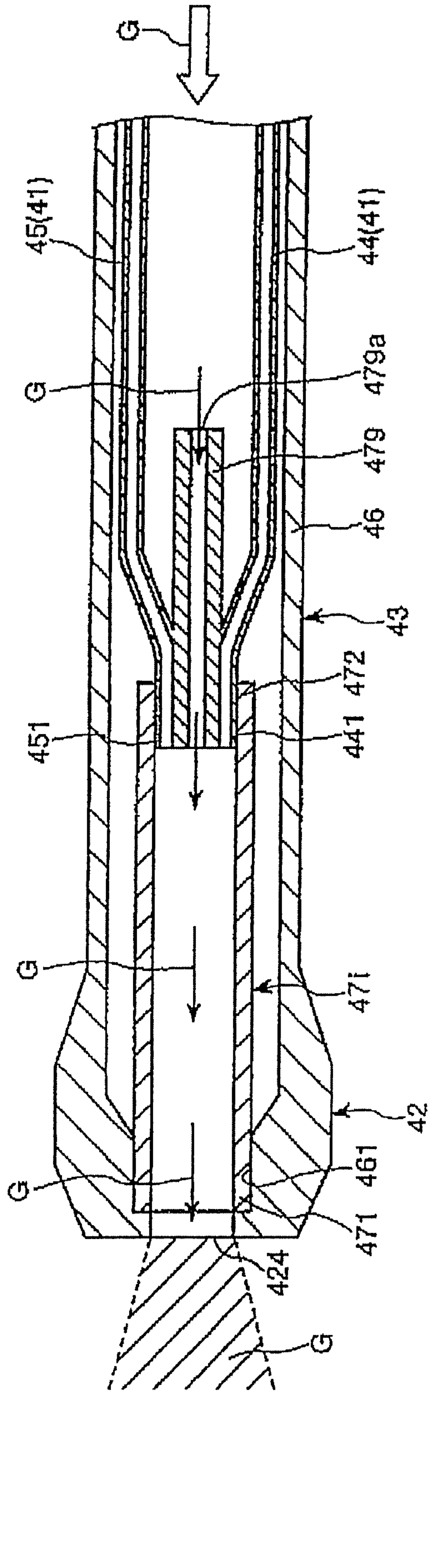
FIG. 13 is a plan view of the distal end part of the nozzle of a sprayer according to a further embodiment.

FIG. 13 illustrates the distal end part of the nozzle in a sprayer according to another embodiment.

The description below of this embodiment of the sprayer focuses primarily upon the differences between this embodiment and the embodiments described above. Features associated with this embodiment that are the same as those associated with the embodiments described above are identified by common reference numerals and a detailed description of such features is not repeated.

This embodiment is the same as the first embodiment except for differences in the configuration of the merge part.

The nozzle 4*i* shown in FIG. 13 includes a tubular part 479 projecting in a tubular form and in a proximal direction from the proximal end part 472 of the merge part 47*i*. Thus, the tubular part 479 projects in the upstream direction toward the proximal end side. The tubular part 479 includes a proximal end opening part 479*a* open into the third flow path 46, and functions as a vent for allowing the gas G which has passed through the third flow path 46 to flow into the merge part 47*i*.

Due to the presence of the tubular part 479 having this configuration, the gas G can flow into the merge part 47*i* via the tubular part 479, and further the liquid mixture in the merge part 47*i* can be relatively reliably inhibited or prevented from involuntarily leaking in the third flow path 46.

As an alternative to the arrangement shown in FIG. 13, the tubular part 479 may be connected to the gas cylinder 300*b*.

The sprayer disclosed here has been described by way of various illustrated embodiments. However, respective parts forming the sprayer can be replaced with others capable of exerting the same or similar functions or operational attributes. Further, additional features may be added to the illustrated embodiments of the sprayer.

Further, it is within the disclosure here to combine disclosed features from different embodiments in the same sprayer. The sprayer may thus be a combination of two or more configurations (features) of the respective embodiments.

Further, the vent or through opening formed in the liquid flow path is not limited to the small hole. The vent or through hole may also take the form of a through slit.

Still further, in the inner surface of the merge part, spiral grooves may be formed. This promotes stirring of the liquids at the merge part.

The principles, embodiments and modes of operation of the sprayer disclosed here have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A sprayer comprising a first liquid supply containing a first liquid;

a second liquid supply containing a second liquid, the first and second liquids having liquid compositions different from one another;

a nozzle comprising a nozzle main body and a nozzle head connected to one another; the nozzle head comprising an ejection port passing through a distal end wall at a distal end of the nozzle head; the nozzle body comprising a first tube, a second tube and a third tube; the first tube possessing a lumen forming a first liquid flow path in fluid communication with the first liquid supply; the second tube possessing a lumen forming a second liquid flow path in fluid communication with the second liquid supply;

the third tube possessing a lumen forming a gas path connectable to a gas source;

a fourth tube constituting a tubular merge part possessing a lumen open at a distal end of the fourth tube, the fourth tube being positioned in the lumen of the third tube, the distal end of the fourth tube contacting the distal end wall of the nozzle head with the lumen of the fourth tube opening into the ejection port; the first tube comprising a distal end; the second tube comprising a distal end the distal end of the first tube and the distal end of the second tube being connected to the fourth tube, with the lumen of the first tube and the lumen of the second tube in communication with the lumen of the fourth tube so that the first and second liquids are mixed together in the fourth tube; and a vent disposed at a point upstream of the distal end of the fourth tube and downstream of the tubular merge part of the fourth tube to introduce the gas into the lumen of the fourth tube; and/or disposed at a point upstream of the distal end of the second tube to introduce the gas into the lumen of the second tube.

2. The sprayer according to claim 1, wherein the vent is a through hole passing through a wall of the tubular merge part.

3. The sprayer according to claim 1, wherein the first tube and the second tube are positioned inside the third tube.

4. The sprayer according to claim 3, wherein an outer surface of the first and second tubes is spaced from an inner surface of the third tube so that a gap exists between the outer surfaces of the first and second tubes and the inner surface of the third tube.

5. The sprayer according to claim 1, wherein the vent is a through hole passing through a wall of the first tube.

6. The sprayer according to claim 5, wherein the distal end of the second tube is positioned distally of the distal end of the first tube.

7. The sprayer according to claim 5, further comprising a through hole passing through a wall of the second tube.

8. The sprayer according to claim 1, further comprising a tubular part extending in a proximal direction from the merge part, the tubular part possessing an opening part forming the vent.

9. The sprayer according to claim 1, wherein the first liquid supply is a first syringe, and the second liquid supply is a second syringe.

10. The sprayer according to claim 1, comprising a valve body positioned in a through hole communicating with the gas path.

11. A sprayer comprising:

supply means for separately supplying a first liquid and a second liquid comprising different liquid compositions;

a nozzle comprising an outer tube, the nozzle also comprising a first liquid flow path in fluid communication with the supply means and along which the first liquid flows, the nozzle also comprising a second liquid flow path in fluid communication with the supply means and along which the second liquid flows, the nozzle also comprising a gas flow path for gas flow, the nozzle also comprising an inner tube possessing an interior, the inner tube being connected to the first flow path and the second flow path so that the first flow path and the second flow path merge together into the interior of the inner tube to mix together, in the interior of the inner tube, the first liquid flowing along the first liquid flow path and the second liquid flowing along the second liquid flow path to form a mixed liquid;

the inner tube, first flow path, second flow path and gas flow path being positioned in the outer tube;

the nozzle also comprising a distal end wall at a distal end of the outer tube and an ejection port passing through the distal end wall, the inner tube possessing a distal end connected to the distal end wall so the interior of the inner tube opens into the ejection port; and at least one vent communicating the interior of the inner tube with the gas flow path so that the gas passing along the gas flow path flows through the at least one vent and enters the interior of the inner tube.

12. The sprayer according to claim 11, wherein the vent is formed at the merge part.

13. The sprayer according to claim 12, wherein the gas flowing in through the vent becomes bubbles in the mixed liquid in the tube, and stirs the liquid.

14. The sprayer according to claim 11, wherein the vent is formed in at least one of the first flow path and the second flow path.

15. The sprayer according to claim 11, further comprising a proximally extending tubular part possessing an opening part forming the at least one vent.

16. The sprayer according to claim 11, wherein the first flow path includes an open end, and the second flow path includes an open end, the open end of the first flow path and the open end of the second flow path being shifted relative to one another in a longitudinal direction of the first and second liquid flow paths.

17. The sprayer according to claim 11, wherein the nozzle comprises an outer tube and two inner tubes positioned inside the outer tube, each inner tube possessing a through hole, the through hole of one of the inner tubes being the first liquid flow path and the through hole of the other inner tube being the second liquid flow path, and wherein a gap exists between outer surfaces of the inner tubes and an inner surface of the outer tube, the gap being the gas flow path.

18. The sprayer according to claim 11, wherein the supply means comprises a syringe having a syringe barrel containing the first liquid, a gasket positioned in the syringe barrel, a plunger connected to the gasket and operable to slidably move the gasket within the syringe barrel.

19. The sprayer according to claim 11, comprising pressure adjusting means for adjusting the pressure in the gas flow path.

20. A method of applying a mixed liquid to a living body comprising:

supplying a first liquid along a first liquid path to an inner tube of a nozzle, the inner tube and the first liquid path being located within an outer tube;

supplying a second liquid along a second liquid path different from the first liquid path to the inner tube of the nozzle to mix the first liquid and the second liquid together in the inner tube to produce a mixed liquid, the first and second liquids comprising different liquid compositions, the second liquid path being located within the outer tube, the nozzle comprising a distal end wall at a distal end of the outer tube, the distal end wall being provided with a through hole forming an ejection port, the inner tube possessing a distal end connected to the distal end wall so an interior of the inner tube opens into the ejection nozzle;

supplying gas to the interior of the tube; and ejecting the mixed liquid and the gas through the distal end of the inner tube and through the ejection port of the nozzle at the living body.

21. The method according to claim 20, wherein the gas is supplied to the inner tube by way of a vent, and the gas flowing through the vent producing bubbles in the mixed liquid and stirring the liquid.

* * * * *